United States Patent
Harding et al.

(10) Patent No.: US 9,587,933 B2
(45) Date of Patent: Mar. 7, 2017

(54) SYSTEM AND METHOD FOR INSPECTING AN OBJECT

(71) Applicant: General Electric Company, Schenectady, NY (US)

(72) Inventors: Kevin George Harding, Niskayuna, NY (US); Joseph Benjamin Ross, Cincinnati, OH (US); Esmaeil Heidari, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 17 days.

(21) Appl. No.: 14/820,640

(22) Filed: Aug. 7, 2015

(65) Prior Publication Data
US 2017/0038199 A1    Feb. 9, 2017

(51) Int. Cl.
| | |
|---|---|
| *G01B 11/26* | (2006.01) |
| *G01B 11/27* | (2006.01) |
| *G01N 21/956* | (2006.01) |

(52) U.S. Cl.
CPC ..... *G01B 11/272* (2013.01); *G01N 21/95607* (2013.01)

(58) Field of Classification Search
CPC ........ G01N 3/08; G01N 23/04; G01B 11/165; G01B 11/254; G02B 23/2407; G01D 5/38; A61B 6/06; G01M 11/0264
USPC ................ 356/605–614, 399–401, 376, 618; 73/822; 382/152
See application file for complete search history.

(56) References Cited

U.S. PATENT DOCUMENTS

| | | | | |
|---|---|---|---|---|
| 4,568,189 | A |   | 2/1986 | Bass et al. |
| 5,052,807 | A |   | 10/1991 | Juday |
| 5,075,560 | A | * | 12/1991 | Greivenkamp, Jr.   G01B 11/026    250/237 G |
| 5,075,562 | A | * | 12/1991 | Greivenkamp, Jr.   G01B 11/026    250/237 G |
| 5,307,153 | A | * | 4/1994 | Maruyama ......... G01B 11/2527    356/604 |
| 5,406,375 | A | * | 4/1995 | Brandstetter ...... G01M 11/0264    356/124 |

(Continued)

OTHER PUBLICATIONS

Dean et al., "Shark-Skin Surfaces For Fluid-Drag Reduction in Turbulent Flow: A Review". Philosophical Transactions A, vol. 368, 2010, 33 Pages.

*Primary Examiner* — Tarifur Chowdhury
*Assistant Examiner* — Isiaka Akanbi
(74) *Attorney, Agent, or Firm* — Paul J. DiConza

(57) ABSTRACT

A method involves receiving a test image of at least a portion of a test object which includes a test moiré pattern generated by superposing one or more reference gratings on one or more subject gratings. The method further involves analyzing one or more test beat lines in the test moiré pattern and calculating one or more test values based on the analysis of the one or more test beat lines. The one or more test values are a function of one or more rotational angles corresponding to the one or more subject gratings and a shape of at least the portion of the test object. The method also involves calculating one or more angular errors of the one or more subject gratings based on the one or more test values and one or more template values and sending a notification based on the one or more angular errors.

20 Claims, 5 Drawing Sheets

(56) References Cited

U.S. PATENT DOCUMENTS

| | | | |
|---|---|---|---|
| 5,732,163 A * | 3/1998 | Brandstetter | G01D 5/38 356/605 |
| 6,336,771 B1 | 1/2002 | Hill | |
| 6,810,601 B2 | 11/2004 | Tondorf | |
| 7,017,274 B2 | 3/2006 | Stobbe | |
| 7,088,458 B1 * | 8/2006 | Wegmann | G01J 9/02 356/124 |
| 7,095,883 B2 * | 8/2006 | Safaee-Rad | G06T 7/001 345/55 |
| 2003/0179373 A1 * | 9/2003 | Magnusson | G01D 5/38 356/328 |
| 2006/0012799 A1 * | 1/2006 | Wegmann | G01J 9/00 356/515 |
| 2008/0032066 A1 | 2/2008 | Stiblert et al. | |
| 2009/0200416 A1 | 8/2009 | Lee | |
| 2011/0024556 A1 | 2/2011 | Cazals et al. | |
| 2011/0141270 A1 * | 6/2011 | Miyake | G01N 21/896 348/125 |
| 2011/0243300 A1 * | 10/2011 | Kaneko | A61B 6/06 378/36 |
| 2012/0168615 A1 | 7/2012 | Hopp et al. | |
| 2012/0176629 A1 | 7/2012 | Allen et al. | |
| 2012/0186337 A1 | 7/2012 | Guichard et al. | |
| 2014/0009579 A1 * | 1/2014 | Sumi | H04N 13/0425 348/46 |
| 2014/0153692 A1 * | 6/2014 | Larkin | G06T 5/10 378/36 |
| 2014/0248453 A1 | 9/2014 | Li et al. | |
| 2014/0272237 A1 | 9/2014 | Roper et al. | |

* cited by examiner

SYSTEM AND METHOD FOR INSPECTING AN OBJECT

BACKGROUND

The technology disclosed herein generally relates to systems and methods for inspecting an object. More specifically, the subject matter relates to inspecting an alignment of one or more gratings on an object.

The advent of new methods such as laser scribing, contacting, shadowing, and the like, have led to the manufacture of gratings on objects (e.g., airfoils, solar cells, and the like). The efficiency and performance of such objects are often directly affected by the alignment of the gratings. For example, airfoils are manufactured with thin riblets (i.e., gratings) on their surface. The efficiency of the airfoil is dependent on the alignment of the riblets because the riblets affect the airflow dynamics and the drag experienced by the airfoil. In another example, solar cells are manufactured with thin gratings on their surfaces. The electrical efficiency of such solar cells is dependent on the alignment of the thin gratings. Current methods of inspecting the alignment of gratings include, for example, manual inspection, inspection using a scanning spot system, and the like. In the manual inspection method, since the gratings are very small, an operator uses a magnifier and visually inspects sections of the object. The manual inspection method is laborious and may lead to errors because such an inspection method is dependent on the quality and experience of the operator. The inspection method using a scanning spot system involves generating a three dimensional map of the object for inspection. This inspection method is very time consuming as the generation of the map often takes a few hours.

Thus, there is a need for an enhanced system and method for inspecting the alignment of gratings on an object.

BRIEF DESCRIPTION

In accordance with one aspect of the present technique, a method involves receiving a test image of at least a portion of a test object. The test image includes a test moiré pattern generated by superposing one or more reference gratings on one or more subject gratings. The method further involves analyzing one or more test beat lines in the test moiré pattern and calculating one or more test values based on the analysis of the one or more test beat lines. The one or more test values are a function of one or more rotational angles corresponding to the one or more subject gratings and a shape of at least the portion of the test object. The method further involves calculating one or more angular errors of the one or more subject gratings based on the one or more test values and one or more template values and sending a notification to a user based on the one or more angular errors.

In accordance with one aspect of the present system, a system includes a communication unit configured to receive a test image of at least a portion of a test object. The test image includes a test moiré pattern generated by superposing one or more reference gratings on one or more subject gratings. The system further includes an analysis unit to analyze one or more test beat lines in the test moiré pattern and calculate one or more test values based on the analysis of the one or more test beat lines. The one or more test values are a function of one or more rotational angles corresponding to the one or more subject gratings and a shape of at least the portion of the test object. The system also includes an error unit configured to calculate one or more angular errors of the one or more subject gratings based on the one or more test values and one or more template values. The system further includes a notification unit configured to send a notification to a user based on the one or more angular errors.

In accordance with another aspect of the present technique, a computer program product encoding instructions is disclosed. The instructions when executed by a processor cause the processor to receive a test image of at least a portion of a test object, wherein the test image includes a test moiré pattern generated by superposing one or more reference gratings on one or more subject gratings. The instructions further cause the processor to analyze one or more test beat lines in the test moiré pattern and calculate one or more test values based on the analysis of the one or more test beat lines. The one or more test values are a function of one or more rotational angles corresponding to the one or more subject gratings and a shape of at least the portion of the test object. The instructions further cause the processor to calculate one or more angular errors of the one or more subject gratings based on the one or more test values and one or more template values. The instructions also cause the processor to send a notification to a user based on the one or more angular errors.

DRAWINGS

These and other features, aspects, and advantages of the present inventions will become better understood when the following detailed description is read with reference to the accompanying drawings in which like characters represent like parts throughout the drawings, wherein.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable and include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged. Such ranges are identified and include all the sub-ranges contained therein unless context or language indicates otherwise.

Figure 1:
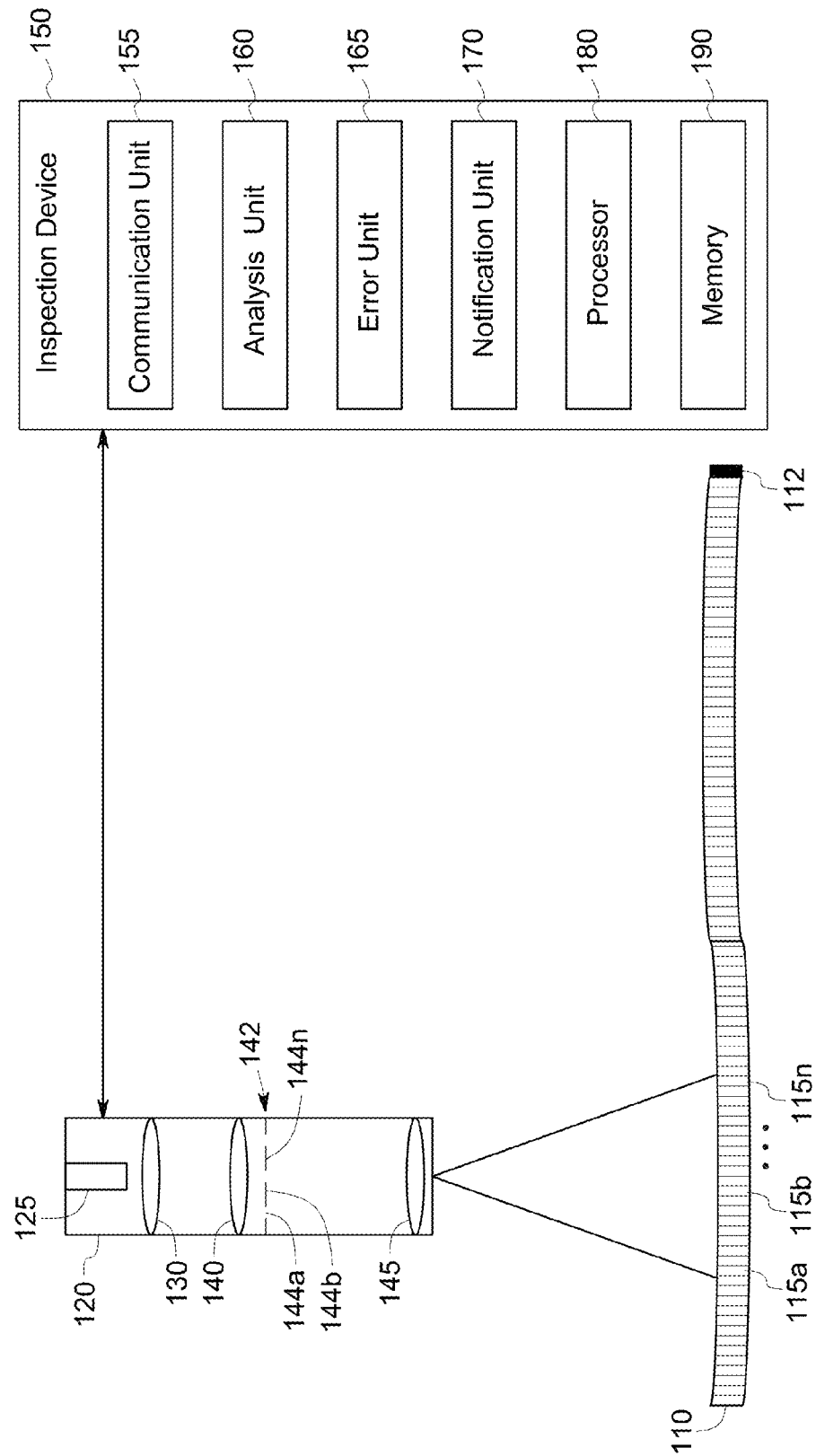
FIG. 1 is a block diagram illustrating a system for inspecting a test object according to one embodiment.

FIG. 1 illustrates an exemplary block diagram of a system 100 for inspecting a test object 110. The system 100 includes an imaging device 120 and an inspection device 150. The imaging device 120 and the inspection device 150 are communicatively coupled to each other via a signal line 195. In one embodiment, the inspection device 150 and the imaging device 120 may be coupled to each other wirelessly. In a further embodiment, the inspection device 150 and the imaging device 120 are coupled via a wired signal line.

As used herein, the term "test object" refers to the object that needs to be inspected by the system 100. The test object 110 includes, for example, an airfoil, or a liquid crystal display, or a thin-film solar cell, or a direct right sensor, or the like. Although in FIG. 1, the test object 110 is illustrated as having a substantially straight or a flat shape without any curvature, in other embodiments, the shape of the test object 110 may be curved or non-planar. The surface of the test object 110 includes a plurality of subject gratings 115a, 115b . . . 115n, where "n" is any integer depending on the number of subject gratings on the test object 110. It should be noted that in the embodiments discussed herein, a letter after a reference number, such as for example, "115a" is a reference to the element having the particular reference number. A reference number in the text without a following letter, such as, for example, "115" is a general reference to any or all instances of the element bearing that reference number. The number of subject gratings 115 may vary depending on the application. In addition, the length, width, and depth of the subject gratings 115 may also vary depending upon the application. Furthermore, the subject gratings 115 do not have to be similar and vary in spacing, size and shape. Although, FIG. 1 illustrates subject gratings 115 on one surface of the object 110 according to one embodiment, in other embodiments, the object 110 may include subject gratings 115 on a plurality of surfaces of the object 110.

In one example, where the test object 110 is an airfoil, the one or more subject gratings 115 may be one or more riblets. The subject gratings 115 may be manufactured on the test object 110, for example, by projecting, shadowing, contacting, laser scribing, and the like. Typically, the width of the one or more subject gratings 115 may be substantially small and may not be directly visible to the human eye. For example, the width of the one or more subject gratings (i.e., riblets) may be less than 50 microns.

The imaging device 120 may be any device configured to generate one or more test images of the test object 110. In the illustrated embodiment, the imaging device 120 includes an image sensor 125, a first imaging lens 130, a second imaging lens 145, a field lens 140, and a reference pattern 142. The reference pattern 142 includes a plurality of reference gratings 144a, 144b . . . 144n, where n is any integer that in some embodiments depends upon the number of reference gratings on the reference pattern 142. The number of reference gratings 144 may vary depending on the application. The image sensor 125 may be any type of sensor configured to generate image data by converting incident light waves into electrical charges. The image sensor 125 may include, for example, semiconductor charge-coupled devices, complementary metal-oxide semiconductor, N-type metal-oxide-semiconductor devices, and the like. The first imaging lens 130, the second imaging lens 145, and the field lens 140 may be any type of optic lenses that are configured to focus and/or direct the light waves from, for example, the test object 110 onto the image sensor 125. Although FIG. 1 illustrates the imaging device 120 as including components such as the image sensor 125, the first and the second imaging lens 130 and 145, a field lens 140, and a reference pattern 142 according to one embodiment, in other embodiments, the components and the configuration of the components in the imaging device 120 may vary.

In one embodiment, the imaging device 120 is configured to generate a test image of at least a portion of the test object 110 including at least some of the plurality of subject gratings 115a, 115b . . . 115n. In such an embodiment, the imaging device 120 is configured to generate the test image of the test object 110 via the reference pattern 142. In this example, the test image is generated by superposing the plurality of reference gratings 144 of the reference pattern 142 on the plurality of subject gratings 115 of the test object 110, and a test moiré pattern is formed in the test image. In a further embodiment, the imaging device 120 is also configured to generate a template image of at least a portion of a template object (not shown) including template gratings (not shown). The number of template gratings may vary depending on the application. As used herein, the terms "template object" and "template gratings" refer to an object and gratings that are devoid of any detectable defects and/or refer to an object and gratings that meet all specifications required by, for example, a user of the test object 110. In such an embodiment, the imaging device 120 is configured to image the template object via the reference pattern 142. Since the template image is generated by superposing the plurality of reference gratings 144 of the reference pattern 142 on the template gratings of the template object, a template moiré pattern is formed in the template image. The imaging device 120 is further configured to transmit the test image and the template image to the inspection device 150 via the signal line 195.

Figure 2:
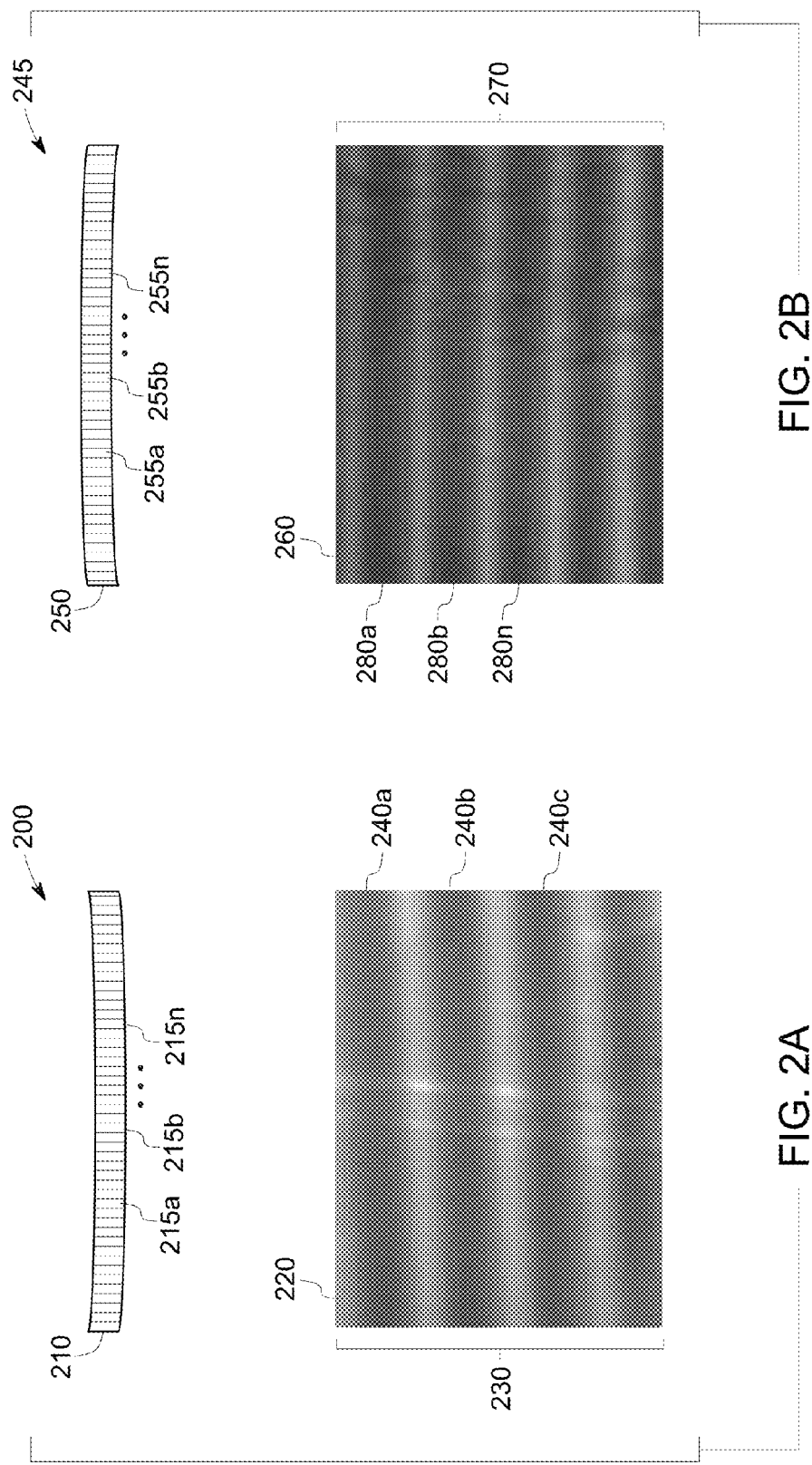
FIG. 2a is a diagrammatical representation illustrating a test object and a test image according to one embodiment.
FIG. 2b is a diagrammatical representation illustrating a template object and a template image according to one embodiment.

Referring now to FIG. 2a, a diagrammatical representation 200 of a test object 210 and a test image 220 is illustrated according to one embodiment. The test object 210 includes a plurality of subject gratings 215*a*, 215*b* . . . 215*n*. An imaging device generates the test image 220 by superposing a plurality of reference gratings on at least a portion of the test object 210. The test image 220 includes a test moiré pattern 230 having a plurality of test beat lines 240*a*, 240*b* . . . 240*n*. Similarly, FIG. 2*b* is a diagrammatical representation 245 illustrating a template object 250 and a template image 260 according to one embodiment. The template object 260 includes a plurality of template gratings 255*a*, 255*b* . . . 255*n*. The imaging device generates the template image 260 by superposing the plurality of reference gratings on at least a portion of the template object 250. The template image 260 includes a template moiré pattern 270 having a plurality of template beat lines 280*a*, 280*b* . . . 280*n*.

Referring back to FIG. 1, the inspection device 150 may be any type of device configured to inspect or analyze the plurality of test gratings 115 on the test object 110. In the illustrated embodiment, the inspection device 150 includes a communication unit 155, an analysis unit 160, an error unit 165, a notification unit 170, a processor 180, and a memory 190. The plurality of units (e.g., the analysis unit 160, the notification unit 170, and the like), the processor 180, and the memory 190 are coupled to a bus (not shown) for communication with each other. In certain other embodiments, the inspection device 150 may be a part of the imaging device 120.

The processor 180 may include at least one arithmetic logic unit, microprocessor, general purpose controller or other processor arrays to perform computations, and/or retrieve data stored in the memory 190. In one embodiment, the processor 180 may be a multiple core processor. The processor 180 processes data signals and may include various computing architectures including a complex instruction set computer (CISC) architecture, a reduced instruction set computer (RISC) architecture, or an architecture implementing a combination of instruction sets. In one embodiment, the processing capability of the processor 180 may support the retrieval of data and transmission of data. In another embodiment, the processing capability of the processor 180 may also perform more complex tasks, including various types of feature extraction, modulating, encoding, multiplexing, and the like. Other type of processors, operating systems, and physical configurations are also envisioned.

The memory 190 may be a non-transitory storage medium. For example, the memory 190 may be a dynamic random access memory (DRAM) device, a static random access memory (SRAM) device, flash memory or other memory devices. The memory 190 may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

The memory 190 stores data that is required for the inspection device 150 to perform associated functions. In one embodiment, the memory 190 stores the units (e.g., communication unit 155, the error unit 165, and the like) of the inspection device 150. In another embodiment, the memory 190 stores one or more template values and an angle threshold. The one or more template values may be generated by the inspection device 150 based on, for example, the template image received from the imaging device 120, Computer Aided Design (CAD) data of the template object, and the like. The angle threshold may be defined by, for example, an administrator of the inspection device 150 based on a-priori data. The one or more template values and the angle threshold are described below in further detail with reference to the error unit 165 and the notification unit 170 respectively.

The communication unit 155 includes codes and routines configured to handle communications between the imaging device 120 and the units of the inspection device 150. In one embodiment, the communication unit 155 includes a set of instructions executable by the processor 180 to provide the functionality for handling communications between the imaging device 120 and the units of the inspection device 150. In another embodiment, the communication unit 155 is stored in the memory 190 and is accessible and executable by the processor 180. In either embodiment, the communication unit 155 is adapted for communication and cooperation with the processor 180 and other units of the inspection device 150.

In one embodiment, the communication unit 155 receives the test image of at least a portion of the test object 110 from the imaging device 120. The communication unit 155 transmits the test image to the analysis unit 160. In another embodiment, the communication unit 155 receives a notification from the notification unit 170. The communication unit 155 transmits the notification to, for example, a display device (not shown) coupled to the inspection device, a user of the inspection device 150, and the like. The notification is described below in further detail with reference to the notification unit 170.

The analysis unit 160 includes codes and routines configured to analyze the test image and calculate one or more test values based on the analysis. The one or more test values are described below in further detail. In one embodiment, the analysis unit 160 includes a set of instructions executable by the processor 180 to provide the functionality for analyzing the test image and calculating the one or more test values based on the analysis. In another embodiment, the analysis unit 160 is stored in the memory 190 and is accessible and executable by the processor 180. In either embodiment, the analysis unit 160 is adapted for communication and cooperation with the processor 180 and other units of the inspection device 150.

In one embodiment, the analysis unit 160 receives the test image of at least a portion of the test object 110. As mentioned above, the test image includes the test moiré pattern generated by superposing the plurality of reference gratings 144 of the reference pattern 142 on the plurality of subject gratings 115 of the test object 110. The analysis unit 160 analyzes a plurality of test beat lines of the test moiré pattern using, for example, beat centroid analysis, beat counting analysis, phase analysis, and Fourier analysis. The analysis unit 160 may identify the plurality of test beat lines of the test moiré pattern by using segmentation algorithms (e.g., edge detection, object recognition, and the like), by identifying zero-crossings of slopes in the test image, by using thresholding algorithms, and the like. The analysis unit 160 then calculates a plurality of test values corresponding to the plurality of test beat lines based on the analysis. The plurality of test values are a function of a plurality of rotational angles of the plurality of subject gratings 115 and the shape of the portion of the test object 110. The rotational angle of a particular subject grating 115 is a measure of the alignment of the particular subject grating 115. Additionally, the rotational angle of a particular subject grating 115 is the angle of the particular subject grating 115 with reference to a datum 112 in the test object 110. Although, FIG. 1 illustrates the datum 112 as one end of the object 110 according to one embodiment, in other embodiments the datum may be any reference point, line, portion of the object 110, and the like, relative to which a rotational angle is determined. In one example where the test object 110 is an airfoil, the rotational angle of a riblet is the angle of the riblet with reference to the base of the airfoil (i.e., datum).

In one embodiment, the analysis unit 160 analyzes the test moiré pattern based on the beat centroid analysis method. In such an embodiment, the analysis unit 160 identifies one or more centroids in each of the plurality of test beat lines of the test moiré pattern. Further, the analysis unit 160 determines data related to the test beat lines, for example, the distance between adjacent centroids, angle of a test beat line between two adjacent centroids, and the like. The analysis unit 160 then calculates a plurality of test values based on the data related to the test beat lines. The beat centroid analysis method is described below in further detail with reference to FIG. 3.

In another embodiment, the analysis unit 160 analyzes the test moiré pattern based on the Fourier analysis method. In such an embodiment, the analysis unit 160 determines the spacing between the plurality of test beat lines (i.e., data related to the plurality of test beat lines). The analysis unit 160 then calculates the plurality of test values based on the spacing between the plurality of test beat lines. In yet another embodiment, the analysis unit 160 analyzes the test moiré pattern based on the phase analysis method. In such an embodiment, the analysis unit 160 calculates the plurality of test values based on changes in at least one of the spacing, a slope, and an angle of the plurality of test beat lines. In yet another embodiment, the analysis unit 160 analyzes the test moiré pattern based on a beat counting analysis method. In such an embodiment, the analysis unit 160 determines a number of test beat lines in the test image. The analysis unit 160 then calculates the plurality of test values using the test beat lines. In each of the embodiments described hereinabove, the analysis unit 160 may be further configured to generate a test map corresponding to the portion of the test object 110. The test map is a three-dimensional representation that maps the plurality of test values with the portion of the test object 110 represented in the test image. The analysis unit 160 is further configured to transmit the plurality of test values and the test map to the error unit 165.

In one embodiment, the analysis unit 160 receives the template image of at least a portion of the template object from the imaging device 120 via the communication unit 155. As mentioned above, the template image includes the template moiré pattern having a plurality of template beat lines. The number of template beat lines may vary depending on the application. Similar to the analysis of the one or more test beat lines to calculate the one or more test values described above, the analysis unit 160 analyzes the plurality of template beat lines and then calculates the plurality of template values. The plurality of template values is a function of the plurality of rotational angles of the template gratings and a shape of the portion of the template object. The rotational angle of a particular template grating is the angle of the particular template grating with reference to a datum in the template object. For the purpose of clarity and convenience, the plurality of rotational angles of the plurality of template gratings are herein referred to as a plurality of desired angles. The analysis unit 160 may further generate a template map corresponding to the portion of the template object. The template map is a three-dimensional representation that maps the plurality of template values with the portion of the template object. The analysis unit 160 may be further configured to store the plurality of template values and the template map in the memory 190.

The error unit 165 includes codes and routines configured to calculate a plurality of angular errors of the plurality of subject gratings 115. In one embodiment, the error unit 165 includes a set of instructions executable by the processor 180 to provide the functionality for calculating the plurality of angular errors of the plurality of subject gratings 115. In another embodiment, the error unit 165 is stored in the memory 190 and is accessible and executable by the processor 180. In either embodiment, the error unit 165 is adapted for communication and cooperation with the processor 180 and other units of the inspection device 150.

In one embodiment, the error unit 165 receives the plurality of test values corresponding to at least the portion of the test object 110. The error unit 165 calculates the plurality of angular errors of the plurality of subject gratings 115 based on the plurality of test values and the plurality of template values. The error unit 165 receives the plurality of template values from the memory 190. As discussed above, the plurality of template values may be generated by the inspection device 150 based on, for example, CAD data of the template object, the template image received from the imaging device 120 prior to receiving the test image, and the like. The plurality of template values received from the memory 190, is representative of a portion of the template object that corresponds to the plurality of test values. The error unit 165 calculates the plurality of angular errors by subtracting the plurality of test values from the plurality of template values. In a further embodiment, the error unit 165 may receive the test map that is representative of the plurality of test values and the template map that is representative of the plurality of template values. In such an embodiment, the error unit 165 calculates the plurality of angular errors by subtracting the test map from the template map.

In another embodiment, the error unit 165 receives the test image including the test moiré pattern from the imaging device 120 via the communication unit 155. The error unit 165 then calculates the plurality of angular errors of the plurality of subject gratings 115 based on the plurality of test beat lines in the test image. In such an embodiment, the error unit 165 identifies at least one intersection in the test image based on, for example, edge detection algorithms, object segmentation algorithms, and the like. The intersection in the test image is representative of an area in the test object 110 which is devoid of any subject gratings. The error unit 165 then further identifies a first set of test beat lines on a first side of the intersection and second set of test beat lines on a second side of the intersection. The error unit 165 then calculates the angular error of the plurality of subject gratings 115 based on a first number of the first set of test beat lines and a second number of the second set of test beat lines.

For example, the error unit 165 calculates a difference between the first number of the first set of test beat lines and the second number of the second set of test beat lines. The error unit 165 then calculates the angular error of the subject gratings 115 by using a look-up table that maps the difference between the first number of the first set of test beat lines and the second number of the second set of test beat lines with the angular error of the plurality of subject gratings 115. The look-up table may be generated by, for example, an administrator of the inspection device 150 based on a-priori data stored in the memory 190. In the illustrated embodiment, the error unit 165 determines an angular error of the subject gratings 115 based on a single intersection. In other embodiments, the error unit 165 may be configured to identify a plurality of intersections in the test image and calculate a plurality of angular errors corresponding to the subject gratings 115 meeting each of the plurality of intersections. In either embodiment, the error unit 165 is configured to transmit the plurality of angular errors corresponding to the plurality of subject gratings 115 of the test object 110 to the notification unit 170.

The notification unit 170 includes codes and routines configured to generate and send a notification to a user of the inspection device 150. In one embodiment, the notification unit 170 includes a set of instructions executable by the processor 180 to provide the functionality for generating and sending a notification to the user of the inspection device 110. In another embodiment, the notification unit 170 is stored in the memory 190 and is accessible and executable by the processor 180. In either embodiment, the notification unit 170 is adapted for communication and cooperation with the processor 180 and other units of the inspection device 150.

The notification unit 170 receives the plurality of angular errors corresponding to the plurality of subject gratings 115 of at least a portion of the test object 110. The notification unit 170 is configured to generate graphical data for providing a notification to, for example, a user of the inspection device 110. The notification may include a permit message or a warning message based on the plurality of angular errors. In one embodiment, the notification unit 170 transmits the graphical data to a display device (not shown). In such an embodiment, the display device renders the graphical data and displays the notification. In another embodiment, the notification unit 170 transmits the notification to a user via, for example, an e-mail, a short messaging service, a voice message, and the like.

In one embodiment, the notification unit 170 determines whether each of the plurality of angular error exceeds an angle threshold. The notification unit 170 receives the angle threshold from the memory 190. As mentioned above, the angle threshold may be defined by, for example, an administrator of the inspection device 150 based on a-priori data. The notification unit 170 determines that the alignment of the one or more subject gratings 115 are correct, if the plurality of angular errors corresponding to the plurality of subject gratings 115 are within the angle threshold. The notification unit 170 then generates graphical data for providing a notification including a permit message to the user. In one example, the notification unit 170 receives two angular errors corresponding to two subject gratings 115*a* and 115*b* as 0.65 degrees and 0.5 degrees respectively. The notification unit 175 determines that the alignment of the two subject gratings 115*a* and 115*b* are correct since the respective angular errors are within the angle threshold of one degree. In such an example, the notification unit 170 generates a notification including a permit message stating "The gratings of the test object are properly aligned."

In another embodiment, the notification unit 170 determines that the plurality of subject gratings 115 are misaligned if the plurality of angular errors corresponding to the plurality of subject gratings 115 exceed the angle threshold. The notification unit 170 then generates graphical data for providing a notification including a warning message to the user. In one example, the notification unit 170 receives an angular error corresponding to two subject gratings 115*b* and 115*n* as 0.5 degrees and 3.5 degrees respectively. The notification unit 175 determines that the alignment of subject grating 115*n* is defective since the corresponding angular error exceeds the angle threshold of one degree. In such an example, the notification unit 170 generates a notification including a warning message stating "The gratings of the test object are misaligned—kindly discard the test object and repair the device for creating the gratings on the test object."

In one embodiment, the notification unit 170 further determines the location of each of the plurality of subject gratings 115 that is misaligned. In such an embodiment, the notification unit 170 generates the notification based on the plurality of locations. In one example, the notification unit 170 determines that the angular errors of three subject gratings 115*a*, 115*b*, and 115*n* are misaligned. In such an example, if the three subject gratings 115*a*, 115*b*, and 115*n* are located proximate to each other or within a threshold distance from each other, then the notification unit 170 infers that the efficiency of the test object 110 is lowered. Thus the notification unit 170 generates a notification including a warning message. In the above example, if the distance between the three subject gratings 115*a*, 115*b*, and 115*n* exceeds a distance threshold, the notification unit 170 infers that the efficiency of the test object 110 is not affected. Thus the notification unit 170 generates a notification including the permit message. The distance threshold may be defined by, for example, an administrator of the inspection device 150 and stored in the memory 190.

Although, the inspection device 150 is described according to one embodiment as inspecting a portion of a test object 110 based on a single test image, in other embodiments, the inspection 150 device may inspect the entire test object 110 based on a single test image. In some embodiments, the inspection device 150 may be configured to receive a plurality of test images corresponding to the entire test object 110 and inspect, for example, each of the plurality of test images. In such an example, the inspection device 150 may include a plurality of template maps corresponding to the plurality of test images. In another example, the inspection device 150 may be configured to generate a master test image by stitching the plurality of test images and inspect the master test image. In such an example, the inspection device 150 may include a master template map corresponding to the master image.

Figure 3:
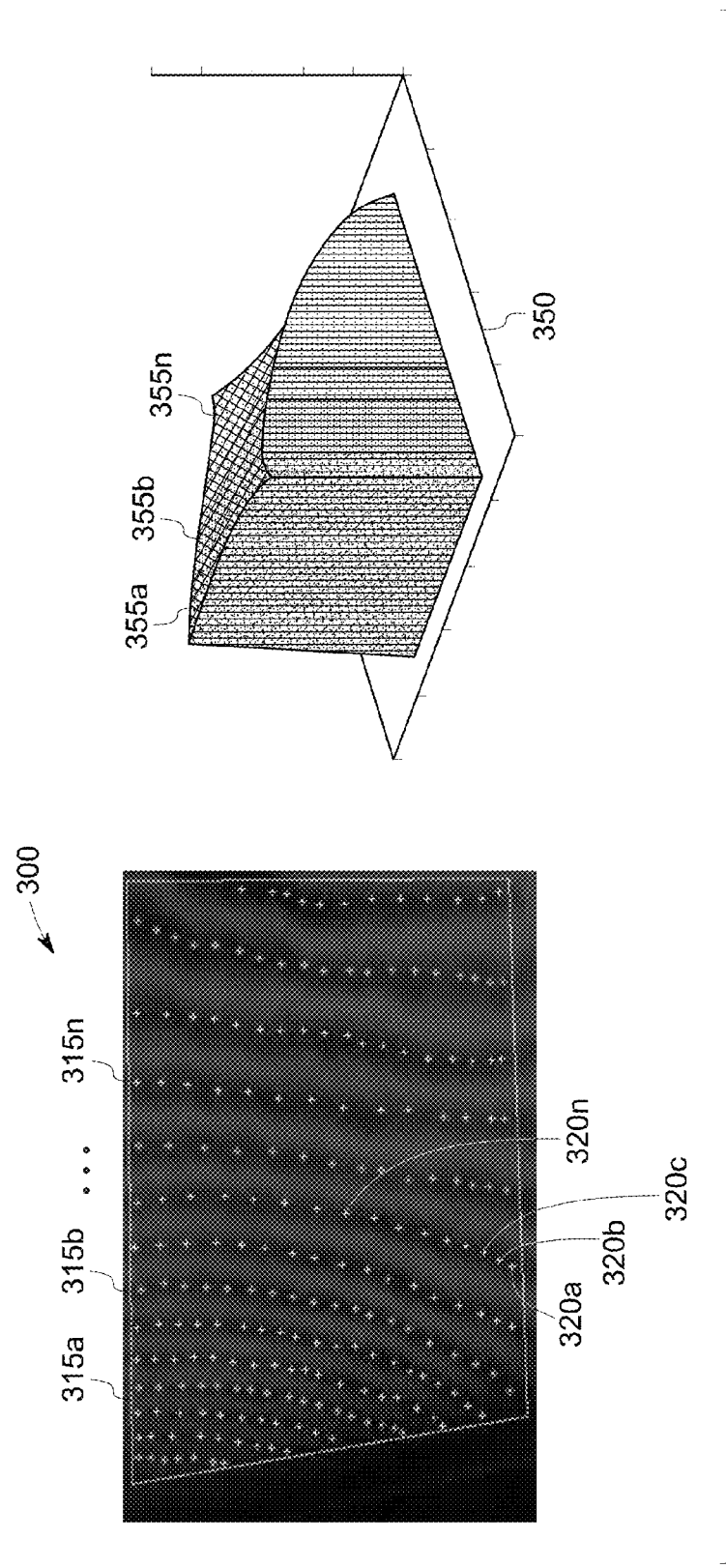
FIG. 3 is a diagrammatical representation illustrating an analysis of a test image according to one embodiment.

Referring now to FIG. 3, a diagrammatical representation 300 of beat centroid analysis of a test image 310 according to one embodiment. The test image 210 includes a moiré pattern including a plurality of test beat lines 315*a*, 315*b* . . . and 315*n*. The analysis unit identifies a plurality of centroids 320*a*, 320*b*, 320*c* . . . and 320*n* in each of the plurality of test beat lines 315. The analysis unit then determines data related to the test beat lines 315 based on the plurality of centroids 320. For example, the analysis unit determines the spacing between adjacent centroids 320*a* and 320*b* and slope of the portion of subject grating between the adjacent centroids 320*a* and 320*b*. Further, the analysis unit calculates a plurality of test values based on the data related to the plurality of test beat lines 315. Furthermore, the analysis unit generates a test map 350 that is a three dimensional representation of a plurality of test values 355*a*, 355*b* . . . and 355*n*.

Figure 4:
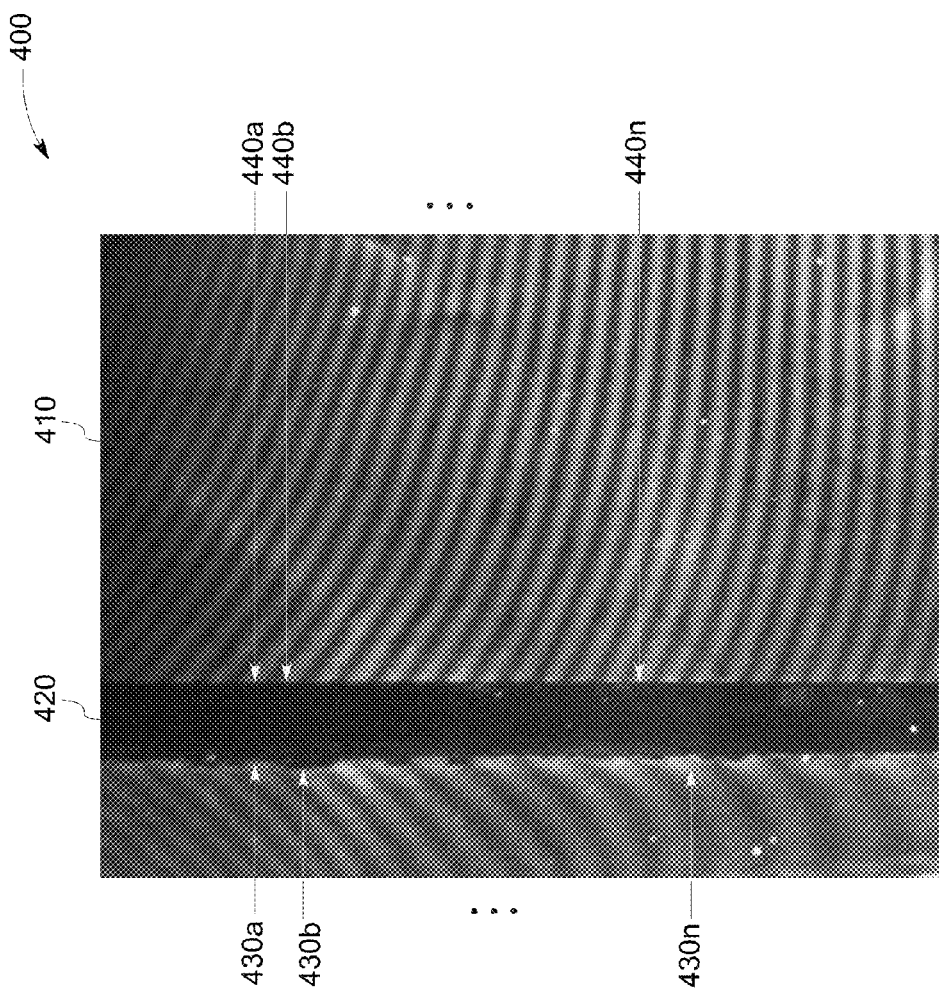
FIG. 4 is a diagrammatical representation illustrating a calculation of an angular error based on a plurality of test beat lines in a test image according to one embodiment.

FIG. 4 illustrates a diagrammatical representation 400 of calculating an angular error based on a plurality of test beat lines in a test image 410 according to one embodiment. The test image 410 includes a test moiré pattern including a plurality of test beat lines. The error unit identifies an intersection 420 in the test image 410. The intersection 420 is representative of an area in the test object that is devoid of subject gratings. The error unit then identifies a first set of test beat lines 430*a*, 430*b* . . . and 430*n* on a first side of the intersection 420. The error unit further identifies a second set of test beat lines 440*a*, 440*b* . . . and 440*n* on a second side of the intersection 420. The error unit then calculates a difference between a number of test beat lines in the first set of test beat lines 430 and a number of test beat lines in the second set of test beat lines 440. The error unit then calculates an angular error of the subject gratings in the portion of the test object based on the difference using, for example, a look-up table stored in the memory.

Figure 5:
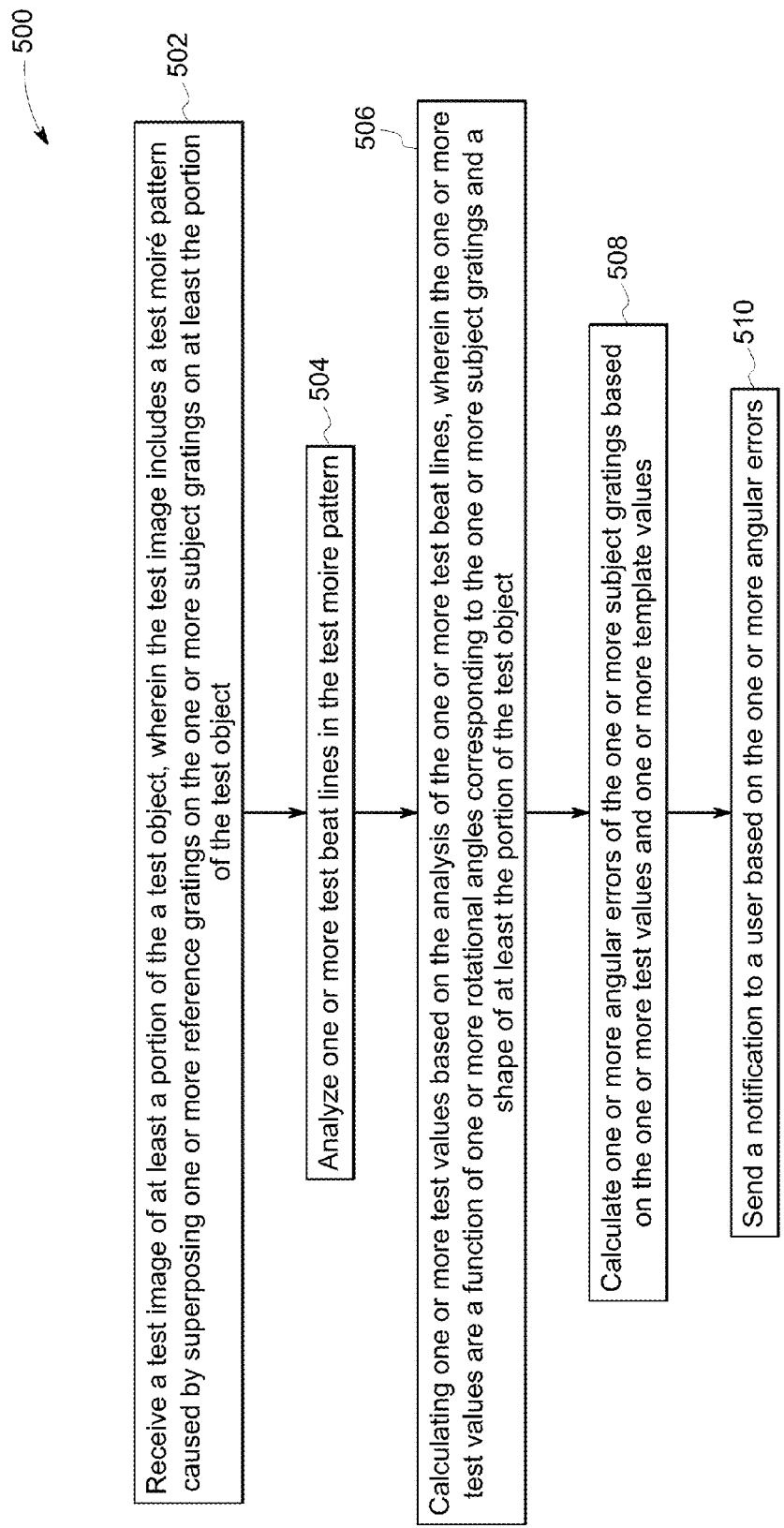
FIG. 5 is a flow diagram illustrating a method for inspecting a test object according to one embodiment.

FIG. 5 is a flow diagram illustrating a method 500 for inspecting a test object according to one embodiment. At step 502, a communication unit receives a test image of at least a portion of a test object. The test image includes a test moiré pattern caused by superposing one or more reference gratings on the one or more subject gratings of at least the portion of the test object. For example, the communication unit receives a test image of one or more riblets (i.e., one or more subject gratings) on a portion of an airfoil (i.e., the test object) from an inspection device. At step 504, the analysis unit analyzes one or more test beat lines in the test moiré pattern. For example, the analysis unit analyzes the one or more test beat lines based on a beat centroid analysis method. At step 506, the analysis unit calculates one or more test values based on the analysis of the one or more test beat lines. The one or more test values are a function of one or more rotational angles corresponding to the one or more subject gratings and a shape of at least the portion of the test object.

At step 508, the error unit calculates one or more angular errors of the one or more subject gratings based on the one or more test values and one or more template values. For example, the error unit calculates the one or more angular errors by subtracting the one or more test values from the one or more template values. The one or more template values are a function of one or more desired angles corresponding to one or more template gratings and a shape of a portion of a template object corresponding to the portion of the test object. At step 510, the notification unit sends a notification to a user based on the one or more angular errors. For example, if the one or more angular errors exceed an angle threshold, the notification unit infers that the one or more subject gratings are misaligned and sends a notification including a warning message. In another example, if the one or more angular errors are within the error threshold, the notification unit infers that the one or more subject gratings are aligned correctly and sends a notification including a permit message.

In accordance with the embodiments discussed herein, the inspection of one or more subject gratings on a test object based on moiré patterns may be performed faster in real-time compared to conventional inspection methods. The inspection of the one or more subject gratings based on the one or more angular errors is advantageous since the subtraction of the of the one or more test values from the one or more template values, removes the issues associated with the shape of the test object 110. This is particularly advantageous in the inspection of test object that have a curved shape.

It is to be understood that not necessarily all such objects or advantages described above may be achieved in accordance with any particular implementation. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the technology has been described in detail in connection with only a limited number of implementations, it should be readily understood that the invention is not limited to such disclosed implementations. Rather, the technology can be modified to incorporate any number of variations, alterations, substitutions or equivalent arrangements not heretofore described, but which are commensurate with the spirit and scope of the disclosure. Additionally, while various implementations of the technology have been described, it is to be understood that aspects of the technology may include only some of the described implementations. Accordingly, the inventions are not to be seen as limited by the foregoing description, but are only limited by the scope of the appended claims.

The invention claimed is:

1. A method for inspecting one or more subject gratings on at least a portion of a test object, the method comprising:
   receiving a test image of at least the portion of the test object, wherein the test image comprises a test moiré pattern generated by superposing one or more reference gratings on the one or more subject gratings;
   analyzing one or more test beat lines in the test moiré pattern;
   calculating one or more test values based on the analysis of the one or more test beat lines, wherein the one or more test values are a function of one or more rotational angles corresponding to the one or more subject gratings and a shape of at least the portion of the test object;
   calculating one or more angular errors of the one or more subject gratings based on the one or more test values and one or more template values; and
   sending a notification to a user based on the one or more angular errors.

2. The method of claim 1, wherein the analysis of the one or more test beat lines in the test moiré pattern is based on at least one of a beat centroid analysis, a beat counting analysis, a phase analysis, and a Fourier analysis.

3. The method of claim 1, further comprising:
   generating a template image of at least a portion of a template object, wherein the template image includes a template moiré pattern generated by superposing the one or more reference gratings on one or more template gratings on at least the portion of the template object;
   analyzing one or more template beat lines in the template moiré pattern; and
   calculating the one or more template values based on the analysis of the one or more template beat lines.

4. The method of claim 3, wherein the one or more template values are a function of a shape of at least the portion of the template object and one or more desired angles corresponding to the one or more template gratings.

5. The method of claim 1, wherein calculating the one or more angular errors comprises subtracting the one or more test values from the one or more template values.

6. The method of claim 1, wherein sending the notification to the user comprises:
   determining whether the one or more angular errors exceed an angle threshold; and
   sending the notification comprising a warning message in response to determining that the one or more angular errors exceed the angle threshold.

7. The method of claim 6, further comprising sending the notification comprising the warning message based on one or more locations associated with the one or more angular errors exceeding the angle threshold.

8. The method of claim 6, further comprising sending the notification comprising a permit message in response to determining that the one or more angular errors are within the angle threshold.

9. The method of claim 1, wherein the test object is an airfoil and the one or more subject gratings are one or more riblets.

10. The method of claim 1, further comprising:
identifying an intersection in the test image;
identifying a first set of test best lines from the one or more test beat lines on a first side of the intersection;
determining a first number of the first set of test beat lines;
identifying a second set of test beat lines from the one or more test beat lines on a second side of the intersection;
determining a second number of the second set of test beat lines; and
calculating the one or more angular errors of the one or more subject gratings based on the first and second number of the test beat lines.

11. A system for inspecting one or more subject gratings on at least a portion of a test object, the system comprising:
at least one processor;
a communication unit executable by the at least one processor, the communication unit configured to receive a test image of at least the portion of the test object, wherein the test image comprises a test moiré pattern generated by superposing one or more reference gratings on the one or more subject gratings;
an analysis unit executable by the at least one processor, the analysis unit communicatively coupled with the communication unit and configured to analyze one or more test beat lines in the test moiré pattern and calculate one or more test values based on the analysis of the one or more test beat lines, wherein the one or more test values are a function of one or more rotational angles corresponding to the one or more subject gratings and a shape of at least the portion of the test object;
an error unit executable by the at least one processor, the error unit communicatively coupled to the analysis unit and configured to calculate one or more angular errors of the one or more subject gratings based on the one or more test values and one or more template values; and
a notification unit executable by the at least one processor, the notification unit communicatively coupled to the error unit and configured to send a notification to a user based on the one or more angular errors.

12. The system of claim 11, wherein the error unit is further configured to calculate the one or more angular errors by subtracting the one or more test values from the one or more template values.

13. The system of claim 11, wherein the notification unit is further configured to determine whether the one or more angular errors exceed an angle threshold and send the notification comprising a warning message in response to determining that the one or more angular errors exceed the angle threshold.

14. The system of claim 13, wherein the notification unit is further configured to send the notification comprising the warning message based on time delay between the first and second time instants is based on one or more locations associated with the one or more angular errors exceeding the angle threshold.

15. The system of claim 13, wherein the notification unit is further configured to send the notification comprising a permit message in response to determining that the one or more angular errors are within the angle threshold.

16. The system of claim 11, wherein the test object is an airfoil and the one or more subject gratings are one or more riblets.

17. A computer program product comprising a non-transitory computer readable medium encoding instructions that, in response to execution by at least one processor, cause the at least one processor to perform operations comprising:
receive a test image of at least a portion of a test object, wherein the test image comprises a test moiré pattern generated by superposing one or more reference gratings on one or more subject gratings;
analyze one or more test beat lines in the test moiré pattern;
calculate one or more test values based on the analysis of the one or more test beat lines, wherein the one or more test values are a function of one or more rotational angles corresponding to the one or more subject gratings and a shape of at least the portion of the test object;
calculate one or more angular errors of the one or more subject gratings based on the one or more test values and one or more template values; and
send a notification to a user based on the one or more angular errors.

18. The computer program product of claim 17, further causing the processor to perform operations comprising determining whether the one or more angular errors exceed an angle threshold and sending the notification comprising a warning message in response to determining that the one or more angular errors exceed the angle threshold.

19. The computer program product of claim 17, further causing the processor to perform operations comprising sending the notification comprising the warning message based on one or more locations associated with the one or more angular errors exceeding the angle threshold.

20. The computer program product of claim 17, further causing the processor to perform operations comprising sending the notification comprising the warning message based on one or more locations associated with the one or more angular errors exceeding the angle threshold.

* * * * *